United States Patent [19]

Puro

[11] 4,395,824

[45] Aug. 2, 1983

[54] WIRE CUTTING TOOL PARTICULARLY FOR ORTHODONTISTS

[75] Inventor: Nicholas S. Puro, Upper Saddle River, N.J.

[73] Assignee: Micro Dent Industries, Inc., Hawthorne, N.J.

[21] Appl. No.: 347,571

[22] Filed: Feb. 10, 1982

[51] Int. Cl.$^3$ ............................................. B26B 13/06
[52] U.S. Cl. ..................................................... 30/134
[58] Field of Search .......................... 30/134, 135, 124

[56] References Cited

U.S. PATENT DOCUMENTS

| | | | |
|---|---|---|---|
| 594,072 | 11/1897 | Forde | 30/134 |
| 1,123,929 | 1/1915 | Russell | 30/134 |
| 2,012,648 | 8/1935 | Wheeler | 30/134 |
| 2,086,081 | 7/1937 | Hollenbeck | 30/134 |
| 3,364,573 | 1/1968 | Hope | 30/124 |
| 3,555,677 | 1/1971 | Cusato | 30/134 |
| 3,783,875 | 1/1974 | Winshel | 30/134 X |
| 3,802,074 | 4/1974 | Hoppe | 30/134 |
| 3,922,781 | 12/1975 | Tippy | 30/124 |

Primary Examiner—Jimmy C. Peters
Attorney, Agent, or Firm—Ralph R. Roberts

[57] ABSTRACT

A plier-type wire cutting tool providing a shear cut of wire such as is used by orthodontists. This wire is used with appliances mounted in the mouth of a patient. This plier is a box-type tool with pivotally connected jaw and handle portions with one jaw having a leaf spring secured to said jaw. This leaf spring is bent at right angles with the short leg of the leaf spring mounted in a slot in the jaw. The other leg of the leaf spring is disposed so as to be movable in a relief formed in this jaw and with this extending leaf portion engaging and retaining said wire that is between the shelf of the opposing jaw and the leaf spring. The cutting edges of the tool are moved toward, to and past each other to cut a wire therebetween with the severed end gripped by the leaf spring and shelf until the jaw ends are moved apart. The shelf and extending leaf portion may be as much as fifty thousandths of an inch apart so that initial engagement of the wire is assured from fifty thousandths of an inch to as little as ten thousandths of an inch and no bending of the wire occurs.

17 Claims, 15 Drawing Figures

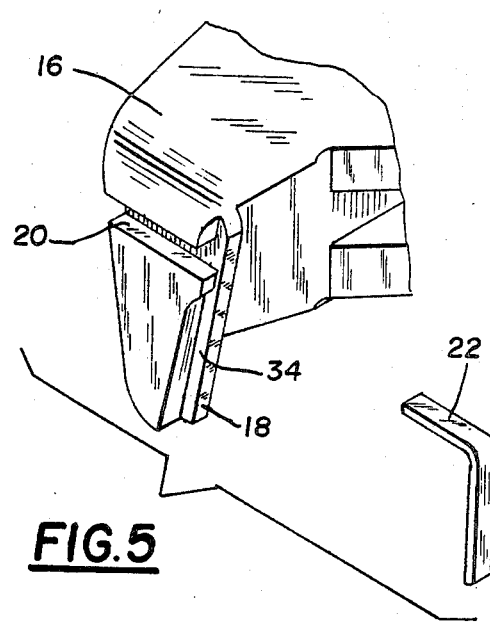
FIG. 5
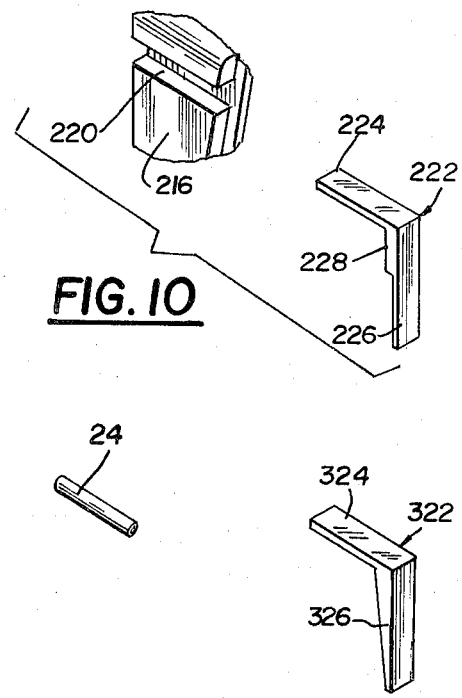
FIG. 10
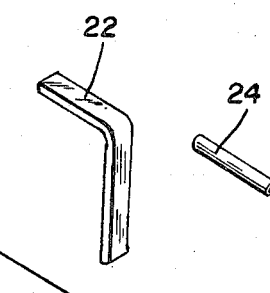
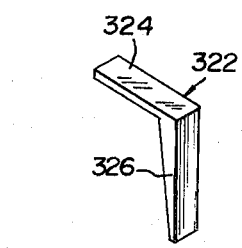
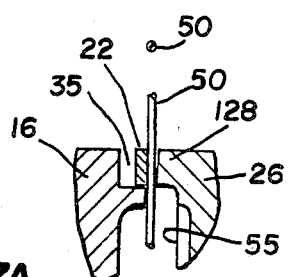
FIG. 7A
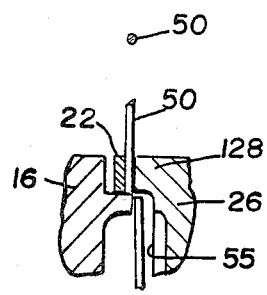
FIG. 11
FIG. 7B
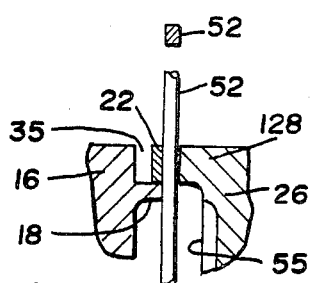
FIG. 8A
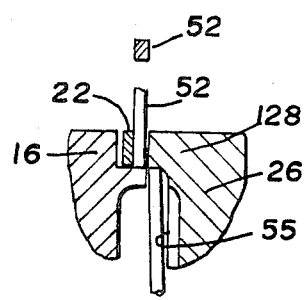
FIG. 8B
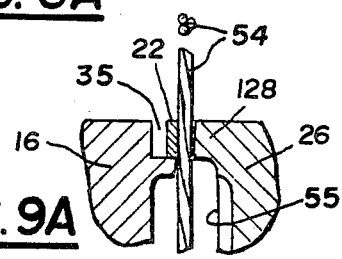
FIG. 9A
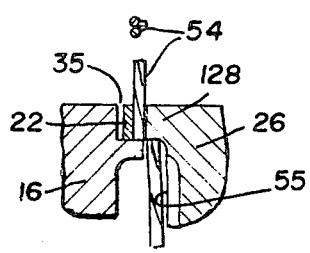
FIG. 9B

WIRE CUTTING TOOL PARTICULARLY FOR ORTHODONTISTS

BACKGROUND OF THE INVENTION

1. Field of the Invention

With reference to the classification of art as established in and by the U.S. Patent Office, this invention is believed to be found in the General Class entitled, "Dentistry" (Class 433) and more particularly in the subclass entitled, "Orthodontics-tool-plier type" (subclass 4).

2. Description of the Prior Art

In the practice of orthodontics, the use of wires to retain, manipulate and adjust teeth into a desired alignment is an established procedure. In particular, clips and the like are cemented to teeth and wires are fed into these clips and attached in a desired manner to cause the teeth to be adjusted to a desired position or condition. In the forming and attaching of these wires, a small surplus of wire at one or both ends is customarily provided as a practical matter. After the completion of the installation of the wire in the mouth, the dentist trims or cuts the surplus end or ends of the wire from the retaining configuration. The wire customarily used in orthodontics is a very high tensile alloy wire usually semi-hard so that in the cutting of this wire by diagonal cutters or nippers the short surplus or unattached end has a tendency to fly. This flying end portion may cause injury to the patient unless the orthodontist takes careful steps to catch or trap it.

In the use of wires in orthodontics, it is of particular note that the cutting of the wire should produce no misalignment or dislodgement of the wire from its installed position. It is also important that the surplus end of the wire, when cut from the installed wire, should not fly into the patient's mouth tissues or throat or in any other manner be a danger to the patient. In the embodiments of the wire cutting tool of this invention said tool jaws are disposed to provide a shear cut and retaining of the severed end. The hardened wire, such as used in the formation of the orthodontic bridge, and the trimmed or cut portion of the wire is gripped and retained by a shelf portion and a leaf spring portion. When the tool is moved to shear cut and to a closed condition it is removed from the mouth and the trimmed portion of the wire is released and discarded from the then opened tool.

A shear-type cut and hold pliers shown in U.S. Pat. No. 3,555,677 as issued Jan. 19, 1971 is of limited utility to dentists because such pliers do not accommodate different sized wires. This is because the gripping faces are positioned and dimensioned with respect to the cutting edges on the blades so as to enable the distal end of the wire to be gripped just as the cut is being completed. The use of larger diameter wire than that for which the cutter is designed results in the wire not being cut through. This is because the gripping jaws engage the wire before the cutting edges come together the requisite amount to achieve and complete the cut. On the other hand, if a wire has a diameter which is less than that for which the cutter is designed, the distal end of the wire flies from the pliers before the gripping jaws can engage it.

In order to have a successful shearing tool, the shearing blades must be mounted so that they slide past each other. Thus, it is essential in such a tool that the means which support the movement of the shearing blades as they pass each other be carefully and accurately made since relative movement of the shearing blades will interfere with the cutting action.

In the wire cutting tool of this invention two patents are particularly noted. U.S. Pat. No. 3,555,677 as issued to Cusato on Jan. 19, 1971 shows a shear cutting tool particularly for wires fifteen thousandths of an inch or less. U.S. Pat. No. 3,922,781 of Dec. 2, 1975 to Tippy shows a diagional cutter in which a wire is disposed to be carried adjacent to the cutting edges of the compression-type cutter and this wire is disposed to grab, engage and retain the small and loose end of the cut wire.

In the course of a pre-Ex search diagional wire cutters were found and among those diagional cutters with holding attachments were U.S. Pat. No. 3,908,268 to Brown as issued on Sept. 30, 1975; U.S. Pat. No. 3,722,093 to Kaupman as issued on Mar. 27, 1973; U.S. Pat. No. 3,740,844 as issued on June 26, 1973 to Rubin; U.S. Pat. No. 3,763,560 as issued to Makkay et al., on Oct. 9, 1973; U.S. Pat. No. 3,777,398 as issued on Dec. 11, 1973 to Routh, Jr.; U.S. Pat. No. 3,842,500 as issued on Oct. 22, 1974 to Cassel and U.S. Pat. No. 4,023,270 as issued May 17, 1977 to Hellerman et al. These all pertain to compression cutting in which the jaws are sharpened and mate to compression cut the wire. Adjacent one or both of the jaws are resilient means for retaining the cut wire. The present invention does not anticipate cutting of the wire by diagional-type cutters. This is commonly called a diagional or compression cut and is not anticipated in the present invention.

SUMMARY OF THE INVENTION

It is an object of this invention to provide, and it does provide, a shear cut wire cutting tool which has a resilient leaf spring secured to one of the jaws and is disposed above and is movable with this jaw to engage and retain a cut wire end as used by orthodontists for ligature and arch wire. Usually this wire is as little as ten thousandths of an inch in diameter up to twenty-five thousandths of an inch in diameter. Also known is rectangular wire and stranded and twisted stainless steel wire which is to be cut after mounting in the mouth.

It is a further object of this invention to provide, and it does provide, a wire cutting tool with a shear-type cut in which one of the jaws is adapted to retain a leaf spring which is parallel to and substantially planar with the top shelf surface of the shear cutter. The other jaw is adapted to effect a shear cut in the wire and the opposed jaw portions provide a shear cut which may be as much as fifty thousandths of an inch apart before the shear cut is made. It is to be noted that the leaf spring is adapted to engage the wire and push the wire against the opposing shelf of the jaw so rather than a tipping of the wire during the cutting and gripping of the wire such as in U.S. Pat. No. 3,555,677 as seen in FIGS. 8, 9 and 10, the wire end is gripped by the leaf spring and urged against the opposing jaw sheft of the opposing jaw prior to, during and after cutting.

Conventionally, the tool of this invention is made with the jaw ends of the plier at an angle which is between sixty and ninety degrees from the plane of the handles. The plier as shown in the drawings (FIGS. 1 and 2) is in substantially full scale and is made particularly for use by orthodontists. The resilient leaf spring is shown with three methods of securing. The first method is a leaf spring at substantially right angles, the short leg of this spring is retained by a roll pin which has a slight expansion and provides a positive securing of the spring. In a second method a similarly bent leaf spring is mounted in a slot in the jaw and is secured by a press fit, brazing, soldering or epoxy cement. The upper jaw not containing the leaf spring may have a small or arcuate recess formed therein so as to urge or guide the wire being cut into a separate position. The leaf spring is also shown as L-shaped with the support integral with the spring so that said support is precisely placed. The jaw may also be straight ground to shear cut the wire. The pliers are shear cut pliers which are conventionally made with a box joint so as to precisely bring the cutting edges into a very close alignment so that a wire is severed by a shear cut.

Conventionally, the tools of this invention are made of stainless steel with the cutting edges made of harder material such as hardened steel or carbide. In use it is anticipated that the shear cut, at the moment of the cutting of the wire, may have the two opposing shelves as much as fifty thousandths of an inch apart but the leaf spring is adapted to move into parallelism with the approaching cutting jaw portion at a distance of approximately ten thousandths of an inch. The resiliency of the leaf spring accommodates a wire of as little as ten thousandths of an inch to as much as forty thousandths of an inch and may be used for wire as much as fifth thousandths of an inch in diameter, which wire is not at the present known to the industry. Tempered wire which is not as hard as the hardened arch wire may also be cut. This tempered wire is usually a stainless steel wire which as a certain amount of spring resiliency so that cutting by a shear cut produces excessive bending of the wire unless a leaf spring such as shown in this invention in provided.

In addition to the above summary the following disclosure is detailed to insure adequacy and aid in understanding of the invention. This disclosure, however, is not intended to cover each concept no matter how it may later be disguised in form or additions of further improvements. For this reason there has been chosen a specific embodiment of a wire cutting tool for orthodontists as adopted for use in the shear cutting of dental wire and showing a leaf spring means for retaining the cut end of the wire and preventing the end from flying. This specific embodiment has been chosen for the purpose of illustration and description as shown in the accompanying drawings wherein:

BRIEF DESCRIPTION OF THE DRAWINGS

FIG. 5 represents an enlarged and exploded isometric view of a plier jaw as in FIGS. 3 and 4 and depicting one configuration of parts used;

FIG. 6 B representing the mounting of the leaf spring and a lift shim at the end of the jaw, the securing of the leg and shim by brazing, soldering or epoxy cement;

FIGS. 7 A and 7 B represent an enlarged view of the shear cut tool at two stages of cutting a small wire. FIG. 7 A shows the small wire prior to the cut and FIG. 7 B shows the small wire after cutting and with the leaf spring retaining said wire after severing;

FIGS. 8 A and 8 B represent the cutting of a larger rectangular wire using the plier-type cutter of FIGS. 7 A and 7 B. FIG. 8 A shows a rectangular or square wire just prior to being cut and 8 B shows the same wire being cut with the fragmentary end retained by the leaf spring;

FIGS. 9 A and 9 B represent the wire-type cutter of FIGS. 7 A and 7 B as adapted for cutting a stranded and twisted wire. 9 A shows a stranded wire prior to a shear cut and FIG. 9 B shows the wire after severing;

FIG. 10 represents an enlarged and exploded isometric view, partly diagrammatic, and showing a plier jaw very similar to the jaw of FIG. 5 but with the support for the movable leg of the leaf spring provided by and integral with this spring, and FIG. 11 represents an isometric view of the L-shaped spring of FIG. 10 with the support made as a taper rather than a formed shoulder.

In the following description and in the claims various details are identified by specific names for convenience. These names are intended to be generic in their application. Corresponding reference characters refer to like members throughout the several figures of the drawings.

EMBODIMENT OF FIGS. 1 AND 2

Figure 1:
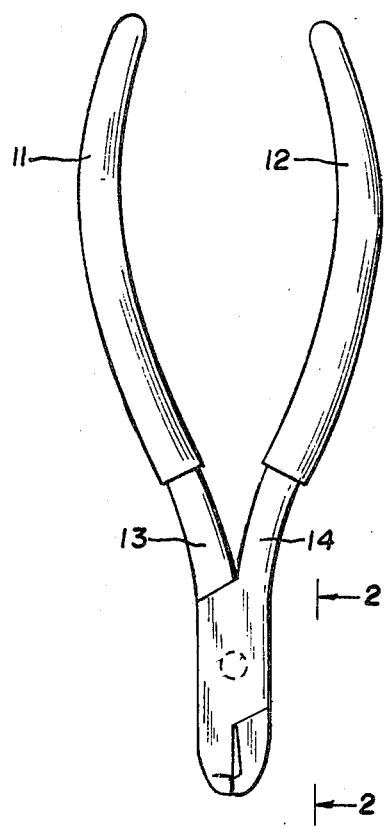
FIG. 1 represents a plan or face view of the plier-type wire cutter of this invention with the jaw ends in a closed condition.
Figure 2:
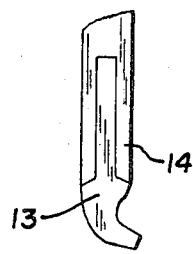
FIG. 2 represents a fragmentary side view of the preferred configuration of the jaw ends of the plier-type cutter of FIG. 1.

Referring now to the drawings and in particular to FIGS. 1 and 2, the jaws forming the wire cutting tool are shaped very similar to that shown in U.S. Pat. No. 3,555,677, above referenced. As shown, plastic handles or grips or sleeves 11 and 12 are applied to the handles 13 and 14. As shown in FIG. 2, the shearing ends of the tool are disposed at a selected angle such as sixty or ninty degrees. A box joint is conventionally employed. The formation of the cutting edges and the jaws are explained hereinafter.

Figure 3:
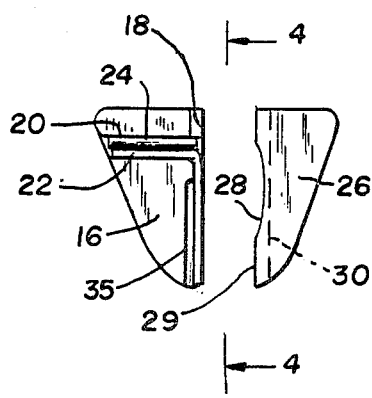
FIG. 3 represents an enlarged and partly fragmentary side view of the wire-type cutting tool jaws with one jaw formed with a small arcuate relief and the leaf spring retained in the other jaw by a pin.
Figure 4:
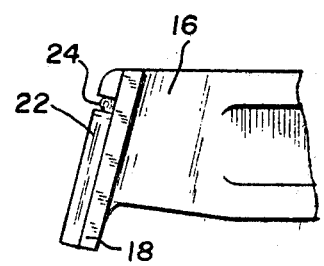
FIG. 4 represents a face view of the jaw with a mounted leaf spring, this view taken on the line 4—4 of FIG. 3 and looking in the direction of the arrows.

Cutting Jaw Ends of FIGS. 3 and 4

In FIGS. 3 and 4 it is noted that one jaw end member is now designated as 16. At substantially right angles to the shear cut ledge and edge 18 is formed a transverse slot 20. A L-shaped leaf spring 22 is of a determined width and is adapted to substantially fill the distal end of the jaw extending from the shear cut ledge 18 to the outer end of the jaw 16. The L-shaped leaf spring 22 is held in place by a pin 24. This may be a roll pin which accommodates small variations in thickness of the spring and secures one leg of the leaf spring 22 tightly in the slot 20. The opposing jaw 26 may be formed with an arcuate shape 28 which encourages the positioning of a wire to be cut. This jaw 26 has a shear cut ledge 29 as seen in FIG. 3. A relief is identified by a dashed line 30.

Exploded View as in FIG. 5

In FIG. 5 is shown a construction of the jaw end 16 in which is mounted the leaf spring 22. This leaf spring is secured in slot 20 by means of a roll pin 24. As seen in other FIGS. to be later described, the slot 20 is made narrower to accommodate only a leg of leaf spring 22. The leg of the leaf spring may be secured in slot 20 by means of epoxy, silver solder or brazing. Adjacent to leaf spring 22 is a shear cut face 34 which is immediately adjacent to and slides by the relief face 30.

Figure 6A:
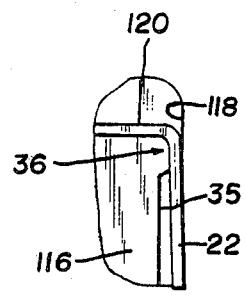
FIGS. 6 A and 6 B represent fragmentary and partly diagrammatic views of the mounting of the leaf spring to the jaws, FIG. 6 A showing the mounting of this leaf spring in a slot in the jaw and with the support integral of the jaw, the securing of the leaf by brazing, soldering or epoxy cement.
Figure 6B:
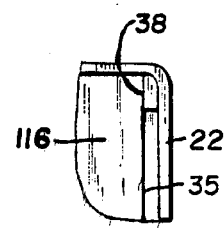

Embodiments of FIGS. 6 A and 6 B

In FIGS. 6 A the shear cut jaw 16 is formed with a slot 120 in which is mounted one leg of the L-shaped leaf spring 22. In this fragmentary view it is to be noted that the short leg of the leaf spring 22 is secured in slot 120 with that area next to the bend of the spring being supported by a protrusion or lump 36 integrally formed in the jaw end 116. This protrusion 36 may also be an insert or otherwise secured shim that provides a support and stop for the leaf spring 22 so that the ledge 18 and the top of the extending leaf spring 22 is substantially in coincidence. A relief 35 provides for a deflected movement of the extending leg of the L-shaped leaf spring 22 when the wire to be cut is pressed thereagainst as in later described embodiments.

In FIG. 6 B the shear cut jaw 116 is formed with no slot and the mounting of the one leg of the L-shaped leaf spring 22 is to an end of the jaw 116. In order to insure the desired positioning of said leaf spring, so as to be substantially coincident with the top of the ledge 118 which is like the ledge 18 above noted, there is provided a shim 38 which is secured to the jaw end as by brazing, soldering or epoxy cement.

The protrusion 36 in FIG. 6 A is depicted as integrally formed and the shim 38 in FIG. 6 B is shown as a separate component but this is not to preclude forming the leaf spring with said positioning support as an integral portion of the spring as in FIG. 10 to be hereinafter more fully described. Whether the leaf spring is made with this protrusion as an extrusion and then the spring is bent, or formed as an L-shaped extrusion or forging is merely a matter of design choice. It is important that the support position the deflecting leg in a manner so that it is not inhibited in its gripping action. The relief 35 allows the free extending leg to move inward or away from the top of the cutting edge of the ledge.

Embodiment of FIGS. 7 A and 7 B

In FIGS. 7 A and 7 B there is shown a typical cutting or severing by means of a shear cut. A wire 50 is a small diameter wire usually of about ten to fifteen thousandths of an inch in diameter. It is to be noted that the leaf spring 22 in FIG. 7 A engages the wire 50 when the jaws 16 and 26 are brought towards each other. The shear cutting ledge 18 and ledge 128 are shown in FIG. 7 A as approaching each other for making a shear cut of the wire 50. In FIG. 7 B the shear cutting ledge 18 and ledge 128 have passed each other to shear cut the wire. The severed or discardable end of the wire 50 is engaged and retained by the leaf spring 22 when and while the shear cutting ledge 18 and ledge 128 pass by each other. It is to be noted that the leaf spring 22 engages the wire 50 to push it and retain it against the approaching ledge 128 after the wire has been severed.

Wire Cutter as seen in FIGS. 8 A and 8 B

Referring now to the drawings and FIGS. 8 A and 8 B, it is to be noted that the same orthodontic tool used for cutting the small wire 50 as in FIG. 7 A and 7 B may also be used to cut square or rectangular wire identified as 52. This square or rectangular wire is usually about twenty-five thousandths of an inch in thickness. This wire is gripped and retained in position as in FIG. 8 A, by leaf spring 22 during the time that the jaw approaches and passes ledge 128. As the jaws 16 and 26 approach each other the leaf spring 22 presses the wire 52 against the shelf or support surface of the ledge 128. In FIG. 8 B the jaws 16 and 26 have moved enough to shear cut the wire and the leaf spring 22 engages and retains the cut end of said wire 52 so as to hold this severed portion against the opposing jaw ledge 128.

Embodiment of FIGS. 9 A and 9 B

Referring next to the drawings and to FIGS. 9 A and 9 B, it is to be noted that the same plier-type tool used for cutting small wire or rectangular wire as above described may also be used for cutting twisted and stranded wire not used in orthodontics. This wire has three twisted strands and is identified as 54 and as provided is approximately twenty-five thousandths of an inch in overall diameter. This wire is of tempered or hardened stainless steel and is sufficient to cut, particularly with diagional-type cutters. Cutting of this wire is easily accomplished by the plier-type shear cutting tool above described. As shown in FIGS. 9 A, jaws 16 and 26 approach each other and the leaf spring 22 retains the wire against the ledge 128. As seen in FIG. 9 B, jaw 18 and ledge 128 have proceeded to and past the cutoff position and the wire 54 has been severed. The free end of the severed end of the wire is retained by the leaf spring 22 urging the severed end of wire 54 against the ledge 128.

Alternate Embodiment of FIG. 10

Referring now to the alternate embodiment of FIG. 10, there is depicted a L-shaped spring generally identified as 222. This spring may be from an extrusion or formed and then bent to the L-shape as shown. A slot 220 formed in jaw 216 is made as a snug or drive fit with secured leg portion 224. Depending and movable leg 226 is formed with a support portion 228. The protrusion 36 seen in FIG. 6 A is not provided in this jaw 216 and the relief 35 providing for movement of the leg 226 is made as a straight cut. The portion 228 provides the desired spacing and support for the L-shaped spring 222.

The deflecting leg moves into relief 35 as shown in FIGS. 7 A, 8 A and 9 A to engage the wire as and when the jaws are brought toward each other and as the wire is cut the deflecting leg engages the wire end and continues engagement thus preventing unwanted flying of a cut wire at the termination of the shear cut. It is to be noted that the cutting ledge and face are straight and hence may be finished as by grinding particularly when and where the cutting portions are made of hardened material such as carbide or tool steel. Epoxy is also contemplated as a securing means for leg 224 in slot 220.

Embodiment of FIG. 11

In FIG. 11 there is shown an alternate construction of the L-shaped spring of FIG. 10. Instead of an abrupt termination of the support 228 of the spring of FIG. 10 it is also contemplated that the deflecting leg may be formed as and with a taper. The inserting leg 324 is sized to be a press fit in slot 220 in jaw 216. This L-shaped spring is identified as 322 and the deflecting leg is identified as 326. This configuration diminishes, if not totally eliminates, fatigue at the end of support 228 in the embodiment of FIG. 10. This configuration particularly lends itself to extrusion and cutoff, or shaping and sizing by die means.

The tool above identified is anticipated to cut very thin wires such as ten or fifteen thousandths of an inch in diameter and also as much as thirty or thirty-five thousandths of an inch in diameter or in thickness. The leaf spring is adapted or is disposed to engage the end of the wire being cut and retain this wire portion against the shelf or a jaw surface during severing. The severing of this wire by shear means is easily accomplished. The wire may be hardened stainless steel or may be a tempered wire conventionally usable in the mouth. The use of wire other than stainless steel is also contemplated. Since the plier-type tool is used in the mouth of the patient it must be rather small in size. The assembly as shown in FIGS. 1 and 2 is of such a size. Whether the leaf spring 22 is secured by a pin, or is a snug fit in the slot and/or secured by epoxy, brazing or silver solder is merely a matter of manufacturing convenience.

The cutting jaw may or may not be made as inserts of hardened steel or carbide. This is also a matter of manufacturing convenience and selection. It is contemplated that the faces of the shear cut are finished and are spaced to slide or pass by each other with the minimum of clearance so as to provide an easy shear cut of the wire. Secured to one of the jaws is a leaf spring 22 parallel to and substantially planar to the top surface of the shear cut ledge 18. The other jaw is adapted to mate with and shear cut an affixed wire. This shear cut has the opposed jaws of the shear cut plier as much as fifty thousandths of an inch apart at the beginning of the shear cut. It is to be noted that the leaf spring is adapted to engage the wire and push the wire against the opposing jaw so that rather than tipping of the wire during cutting and gripping of the wire such as in U.S. Pat. No. 3,556,677 above noted in the description of FIGS. 8, 9 and 10, the cut wire end is gripped by the spring and is urged against the shelf of the opposing jaw. This wire cutting tool is made with jaw ends at an angle which is between sixty and ninety degrees from the plane of the longitudinal axis of the handles. The plier assembly of this invention is shown in the drawings in substantially full scale and is made particularly for use by orthodontists. The resilient leaf spring is shown with four methods for securing. The leaf spring is conventionally of stainless steel tempered to provide the spring bias but certain metal alloys or some of the new plastics which are resistant to sterilization, wear and/or abuse are also contemplated. The spring must not rust and also is required to have the capability to sterilization by heat, chemicals or ultra-violet ray. The first method is with a leaf spring at substantially right angles and secured in a slot in a jaw with the short length of the leaf spring retained by a roll pin which may have a slight expansion by which a positive securing of the leaf spring is made. A second method is similarly bent leaf spring mounted in the slot of the jaw and is secured by brazing or epoxy cement. A third method includes a L-shaped spring having an integral support portion at and on the deflecting leg. The upper jaw not containing the spring may have a small arcuate recess formed therein so as to urge or guide the wire to be cut into a securing or centering position. The ledge is also shown as straight ground to shear cut the wire. A fourth method of securing the leaf spring 22 is attaching said spring to the end of the jaw. Usually this attaching method includes a shim to carry the extending leaf portion of the spring at a pre-established distance above the relief 35. As noted, the upper surface of the leaf spring is substantially in coincidence with the upper surface 18 of the jaw.

It is to be noted that the leaf spring 22 and the relief 35 provided in the jaw end 16 are sized to allow the cutting portions 18 and 128 to engage and then cut a wire from ten to as much as fifth thousandths of an inch in diameter or thickness. The severed end, before and after cutting, is pressed to and against the shelf of the mating jaw. After severing, the wire mounted in the mouth of the patient is pushed by the portion 18 toward the opposite jaw but a relief 55 provided in this jaw is greater than the anticipated thickness of wire to be cut so that as seen in FIGS. 7 A, 7 B, 8 A, 8 B, 9 A and 9 B the attached wire is not gripped.

Terms such as "up", "down", "bottom", "top", "front", "back" "in", "out" and the like are applicable to the embodiments shown and described in conjunction with the drawings. These terms are merely for the purposes of description and do not necessarily apply to the position in which the plier-type cutting tool may be constructed or used.

While particular embodiments of said cutting tool have been shown and described it is to be understood the invention is not limited thereto and protection is sought to the broadest extent the prior art allows.

What is claimed is:

1. A plier-type wire cutting tool particularly for orthodontic use in cutting a wire used with appliances mounted in the mouth of a patient, said wire severed by this tool by a shear cut with one end of the wire retained by the appliance to which it is attached and with the other end, after severing, gripped by a resilient leaf spring carried by one jaw of the tool and by a facing shelf portion of an opposed jaw, said plier-type tool including:
   (a) a pair of plier-type members including handle and jaw portions connected so as to be pivotally movable;
   (b) a pivot joint pin adapted for retaining said plier-type members in a pivotal relationship so that as and when manipulated the jaw portions of the wire cutting tool are moved away and toward each other;
   (c) a shear cutting edge and ledge formed in each jaw end of the tool, said shear cutting edge and ledge portions adapted to approach and slide by each other to shear cut a wire disposed in way of said shear edge cutting portions;
   (d) a leaf spring having a first leg secured to and carried by one of the jaw portions, said leaf spring having a second leg disposed to lay adjacent a shear cutting edge and away from the pivot joint pin, said leaf spring having this second leg as an extending leaf portion movable against a bias of and in said spring, this extending leaf portion disposed a short distance above the jaw portion and substantially parallel to the top surface of the shear cutting edge and ledge in the jaw portion to which it is attached, the jaw portion having a relief formed in the shelf portion to accommodate the extending portion of the leaf spring and with clearance for a desired securing motion and position when and while a wire is being cut, and
   (e) a flat shelf portion formed in the jaw portion opposite the leaf spring, said shelf arranged to engage the wire end and move the wire against the shelf and grip said wire as the shear cutting edges and ledges are moved toward, to and past each other to cut said wire and produce a severed end, the severed end of the wire being gripped between the extending leaf portion and shelf until the jaw portions are moved apart, usually after removal from the mouth of the patient, said flat shelf and extending leaf portion being as much as forty thousandths of an inch apart when and as initial engagement and retention of the wire occurs.

2. A plier-type cutting tool as in claim 1 in which the leaf spring is formed into an L-shaped substantially right angle with said first leg of said leaf spring secured in a slot in the jaw portion, said slot transverse of the shear cutting edge.

3. A plier-type cutting tool as in claim 2 in which said first leg of the leaf spring is secured in said slot by means of a pin.

4. A plier-type cutting tool as in claim 2 in which said first leg of the leaf spring is secured in the slot by brazing, soldering and the like.

5. A plier-type cutting tool as in claim 2 in which said first leg of the leaf spring is secured in the slot by epoxy cement.

6. A plier-type cutting tool as in claim 2 in which the L-shaped spring is formed with a thickened portion adjacent the formed bend or angle and in that extending second leg portion which provides the deflecting leg, this thickened portion provides positioning means disposed to insure that the remaining portion of the second leg is freely movable to and into the relief in the jaw.

7. A plier-type cutting tool as in claim 7 in which the L-shaped spring is an extrusion.

8. A plier-type cutting tool as in claim 6 in which the L-shaped spring is first formed with a thickened portion and then bent to the desired L-shape.

9. A plier-type cutting tool as in claim 1 in which the shelf in the jaw end opposite the leaf spring is made with a shallow deformation to encourage and provide a seating placement of the wire on said shelf during severing.

10. A plier-type cutting tool as in claim 1 in which the leaf spring is formed into a substantially right angle with a first leg of said spring secured to an end of the jaw portion and a support is provided in or to the jaw portion adjacent said end, this support adapted to position an extending second leg of the leaf spring so as to provide the desired leaf spring clearance.

11. A plier-type cutting tool as in claim 10 in which the support providing for the bent leaf spring is a shim secured to the jaw portion.

12. A plier-type cutting tool as in claim 10 in which the leaf spring is formed with unequal leg portions and with the first leg secured to the jaw portion and the second leg free to move toward the relief.

13. A plier-type cutting tool as in claim 10 in which the first leg is secured in a slot in the jaw portion.

14. A plier-type cutting tool as in claim 10 in which the support for the movable leg is formed as an integral portion of the jaw member.

15. A plier-type cutting tool as in claim 10 in which the relief in the jaw for the leaf spring is adjacent to and extends from a support of short extent.

16. A plier-type cutting tool as in claim 14 in which the movable leg containing the integral support portion has a thickened portion extending from the bend a short distance and then the remaining leg portion is at a reduced thickness.

17. A plier-type cutting tool as in claim 14 in which the movable leg containing the integral support portion is formed with a taper extending from the support portion and diminishing from said support portion to the free end.

* * * * *